US008525989B2

(12) United States Patent
Iguchi et al.

(10) Patent No.: US 8,525,989 B2
(45) Date of Patent: Sep. 3, 2013

(54) SPECTROMETER, SPECTROMETRY, AND SPECTROMETRY PROGRAM

(75) Inventors: Kazuya Iguchi, Hamamatsu (JP); Kengo Suzuki, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 222 days.

(21) Appl. No.: 13/000,466

(22) PCT Filed: Jun. 10, 2009

(86) PCT No.: PCT/JP2009/060618
§ 371 (c)(1),
(2), (4) Date: Dec. 21, 2010

(87) PCT Pub. No.: WO2010/001700
PCT Pub. Date: Jan. 7, 2010

(65) Prior Publication Data
US 2011/0098962 A1 Apr. 28, 2011

(30) Foreign Application Priority Data
Jun. 30, 2008 (JP) .................................. 2008-170940

(51) Int. Cl.
*G01J 3/28* (2006.01)
(52) U.S. Cl.
USPC .......................................................... 356/326
(58) Field of Classification Search
USPC ........................................ 356/326, 328, 334
See application file for complete search history.

(56) References Cited

U.S. PATENT DOCUMENTS 3,838,926 A 10/1974 Kato et al.
4,645,340 A * 2/1987 Graham et al. ............... 356/301

(Continued)

FOREIGN PATENT DOCUMENTS

JP 60-230040 11/1985
JP 62-289747 12/1987

(Continued)

OTHER PUBLICATIONS

T. Javorfi et al., "Quantitative spectrophotometry using integrating cavities," Journal of Photochemistry and Photobiology, B: Biology, vol. 82, No. 2, Feb. 1, 2006, pp. 127-131.

(Continued)

*Primary Examiner* — Tarifur Chowdhury
*Assistant Examiner* — Abdullahi Nur
(74) *Attorney, Agent, or Firm* — Drinker Biddle & Reath LLP

(57) ABSTRACT

A spectroscopic measurement apparatus comprises an integrating sphere in which a sample is located, an irradiation light supplying section supplying excitation light via an entrance aperture to the interior of the integrating sphere, a sample container holding the sample in the interior of the integrating sphere, a spectroscopic analyzer dispersing the light to be measured from an exit aperture and obtaining a wavelength spectrum, and a data analyzer performing data analysis of the wavelength spectrum. The analyzer includes a correction data obtaining section which obtains correction data of the wavelength spectrum considering light absorption by the sample container, and a sample information analyzing section which corrects and analyzes the wavelength spectrum to obtain sample information. This realizes a spectroscopic measurement apparatus, a measurement method, and a measurement program which can preferably perform spectroscopic measurement of the sample held by the sample container in the integrating sphere.

11 Claims, 12 Drawing Sheets

(56) References Cited

U.S. PATENT DOCUMENTS

| | | | |
|---|---|---|---|
| 6,870,615 B2 * | 3/2005 | Parks et al. .................. | 356/319 |
| 2002/0197740 A1 | 12/2002 | Hansen et al. | |
| 2003/0120137 A1 | 6/2003 | Pawluczyk | |

FOREIGN PATENT DOCUMENTS

| | | |
|---|---|---|
| JP | H10-142153 | 5/1998 |
| JP | 2001-083094 | 3/2001 |
| JP | 2003-215041 | 7/2003 |
| JP | 2007-033334 | 2/2007 |
| JP | 2007-086031 | 4/2007 |
| JP | 2007-198983 | 8/2007 |
| JP | 2007-236219 | 9/2007 |
| JP | 2009-031015 | 2/2009 |
| JP | 2009-031016 | 2/2009 |
| JP | 2009-074866 | 4/2009 |

OTHER PUBLICATIONS

N. C. Yates et al., "Water-soluble metal naphthalocyanines-near-IR photosensitizers: Cellular uptake, toxicity and photosensitizing properties in nhik 3025 human cancer cells," Journal of Photochemistry and Photobiology, B: Biology, vol. 4, No. 4, Mar. 1, 1990, pp. 379-390.

B. Marcel et al., "Light absorption by aquatic particles in the near-infrared spectral region," Limnology and Oceanography, vol. 47, No. 3, May 3, 2002, pp. 911-915.

N. B. Nelson et al., "Calibration of an integrating sphere for determining the absorption coefficient of scattering suspensions," Applied Optics, vol. 32, No. 33, Nov. 20, 1993, pp. 6710-6717.

* cited by examiner (a)

(b)

(a)

(b)

(a)

(b)

(a)

(b)

SPECTROMETER, SPECTROMETRY, AND SPECTROMETRY PROGRAM

TECHNICAL FIELD

The present invention relates to a spectroscopic measurement apparatus having an integrating sphere, a spectroscopic measurement method performed by using the spectroscopic measurement apparatus, and a spectroscopic measurement program.

BACKGROUND ART

An integrating sphere is used to measure the intensity of light emitted from a sample. The inner wall of the integrating sphere is made out of a coating or a material having a high reflectance and excellent in diffuseness, and light incident on the inner wall surface is multiply diffusely-reflected. Then, the diffused light from the sample enters a photodetector through an exit aperture provided at a predetermined position of the integrating sphere to be detected, and this method can obtain information of light emitting intensity and the like of the sample with high accuracy without depending on a light emission pattern, a light emission angle characteristic, and the like of the sample (for example, refer to Patent Document 1).

An organic EL (electroluminescence) element serves as an example of the sample of a target of measurement using the integrating sphere. The organic EL element is a light emitting element generally having a structure with an anode, an organic layer including a light emitting layer, and a cathode laminated on a substrate made out of glass or a transparent resin material. Photons are generated by holes injected from the anode and electrons injected from the cathode being recombined in the light emitting layer, and the light emitting layer emits light.

In measurement and evaluation of light emission characteristics of the organic EL element, an external quantum efficiency defined by a ratio of the number of photons emitted to the outside of the element to the number of injected electrons, and the like, becomes important. Further, in measurement and evaluation of a luminescent material used in the organic EL element, a luminescence quantum yield (internal quantum efficiency) defined by a ratio of the number of photons of light emitted from the sample to the number of photons of excitation light absorbed by the sample becomes important. A light measurement device using the integrating sphere can be preferably used for evaluation of quantum efficiency of such an organic EL element.

CITATION LIST

Patent Literature

Patent Document 1: Japanese Patent Application Laid-Open No. 2003-215041

SUMMARY OF INVENTION

Technical Problem

In recent years, the importance of evaluating the luminescence quantum yield of a luminescent material used for light emitting elements has been increased to improve a light emitting efficiency of a light emitting element such as an organic EL element in terms of power consumption reductions, in research and development of next-generation displays and next-generation illumination. As the evaluation method of the luminescence quantum yield, there is a method for measuring an absolute luminescence quantum yield of a luminescent material by a photoluminescence (PL) method with a light measurement device having the above-described integrating sphere.

Specifically, in the evaluation of the luminescence quantum yield by the PL method, a sample of a luminescent material located in the integrating sphere is irradiated with excitation light of a predetermined wavelength, and a luminescence quantum yield $\phi_{PL}$ defined by a ratio of photon number of light emission such as fluorescence from the sample to photon number of the excitation light absorbed by the sample is measured. Further, for this quantum yield, it is possible to use a method of obtaining the yield based on the measurement results of a reference measurement of performing a measurement with a sample container located in the integrating sphere without the sample and a sample measurement of performing a measurement with the sample held by the sample container located in the integrating sphere.

The inventors of the present invention have found that, as a result of considering spectroscopic measurement for such a sample, the measurement using the integrating sphere may have the reduced accuracy of sample information obtained by the measurement because the excitation light, the light emitted from the sample, and the like are multi-reflected by the inner wall, to make multiple passes through the sample container. In this case, the influence of a sample container on light absorption cannot be disregarded, so that an error is caused, by wavelength dependency of its absorptance (transmittance) and the like, in the analysis result of the luminescence quantum yield and the like.

The present invention has been made in order to solve the above-described problem, and an object thereof is to provide a spectroscopic measurement apparatus, a spectroscopic measurement method, and a spectroscopic measurement program, which can preferably perform the spectroscopic measurement of the sample held by the sample container in the integrating sphere.

Solution to Problem

In order to achieve the above object, a spectroscopic measurement apparatus according to the present invention comprises: (1) an integrating sphere in which a sample as a measurement object is located, and having an entrance aperture for inputting excitation light with which the sample is irradiated, and an exit aperture for outputting light to be measured from the sample; (2) irradiation light supplying means supplying the excitation light as irradiation light supplied via the entrance aperture to the interior of the integrating sphere; (3) a sample container holding the sample at a predetermined position in the interior of the integrating sphere; (4) spectroscopic means dispersing the light to be measured output from the exit aperture of the integrating sphere and obtaining a wavelength spectrum; and (5) data analyzing means performing data analysis of the wavelength spectrum obtained by the spectroscopic means; wherein (6) the data analyzing means includes: correction data obtaining means obtaining correction data for correcting the wavelength spectrum by considering absorption of at least one of the excitation light and the light to be measured by the sample container; and sample information analyzing means obtaining information of the sample by correcting the wavelength spectrum with the correction data and analyzing the corrected wavelength spectrum.

Further, a spectroscopic measurement method according to the present invention uses a spectroscopic measurement apparatus including: (1) an integrating sphere in which a sample as a measurement object is located, and having an entrance aperture for inputting excitation light with which the sample is irradiated, and an exit aperture for outputting light to be measured from the sample; (2) irradiation light supplying means supplying the excitation light as irradiation light supplied via the entrance aperture to the interior of the integrating sphere; (3) a sample container holding the sample at a predetermined position in the interior of the integrating sphere; and (4) spectroscopic means dispersing the light to be measured output from the exit aperture of the integrating sphere and obtaining a wavelength spectrum, wherein (5) the spectroscopic measurement method performs data analysis of the wavelength spectrum obtained by the spectroscopic means, and comprises: (6) a correction data obtaining step of obtaining correction data for correcting the wavelength spectrum by considering absorption of at least one of the excitation light and the light to be measured by the sample container; and a sample information analyzing step of obtaining information of the sample by correcting the wavelength spectrum with the correction data and analyzing the corrected wavelength spectrum.

Further, a spectroscopic measurement program according to the present invention is applied to a spectroscopic measurement apparatus including: (1) an integrating sphere in which a sample as a measurement object is located, and having an entrance aperture for inputting excitation light with which the sample is irradiated, and an exit aperture for outputting light to be measured from the sample; (2) irradiation light supplying means supplying the excitation light as irradiation light supplied via the entrance aperture to the interior of the integrating sphere; (3) a sample container holding the sample at a predetermined position in the interior of the integrating sphere; and (4) spectroscopic means dispersing the light to be measured output from the exit aperture of the integrating sphere and obtaining a wavelength spectrum, wherein (5) the program makes a computer execute data analysis of the wavelength spectrum obtained by the spectroscopic means, and makes the computer execute: (6) a correction data obtaining process of obtaining correction data for correcting the wavelength spectrum by considering absorption of at least one of the excitation light and the light to be measured by the sample container; and a sample information analyzing process of obtaining information of the sample by correcting the wavelength spectrum with the correction data and analyzing the corrected wavelength spectrum.

In the spectroscopic measurement apparatus, the spectroscopic measurement method, and the spectroscopic measurement program described above, the spectroscopic measurement apparatus is configured by using the integrating sphere which has the aperture for excitation light input and the aperture for light to be measured output and is configured so as to be able to measure the light emission characteristics of the sample by a photoluminescence method, and the spectroscopic means which spectroscopically measures the light to be measured so that the excitation light and the light emitted from the sample can be distinguished by the wavelength spectrum. Then, the correction data considering light absorption by the sample container are prepared for the sample container holding the sample in the integrating sphere, the wavelength spectrum is corrected by the correction data, and then, analysis of the wavelength spectrum and derivation of sample information are performed. This reduces errors caused in the analysis result of the luminescence quantum yield and the like, and allows the spectroscopic measurement for the sample to be performed preferably and accurately, even in the case where the influence of the sample container on light absorption cannot be disregarded.

Advantageous Effects of Invention

In accordance with the spectroscopic measurement apparatus, the measurement method, and the measurement program of the present invention, correction data considering light absorption by the sample container for holding the sample in the integrating sphere are prepared for the spectroscopic measurement apparatus having the integrating sphere and the spectroscopic means, the wavelength spectrum is corrected by the correction data, and then, analysis of the wavelength spectrum and derivation of sample information are performed, and this allows the spectroscopic measurement for the sample to be performed preferably, even in the case where the influence of the light absorption by the sample container cannot be disregarded.

DESCRIPTION OF EMBODIMENTS

Figure 1:
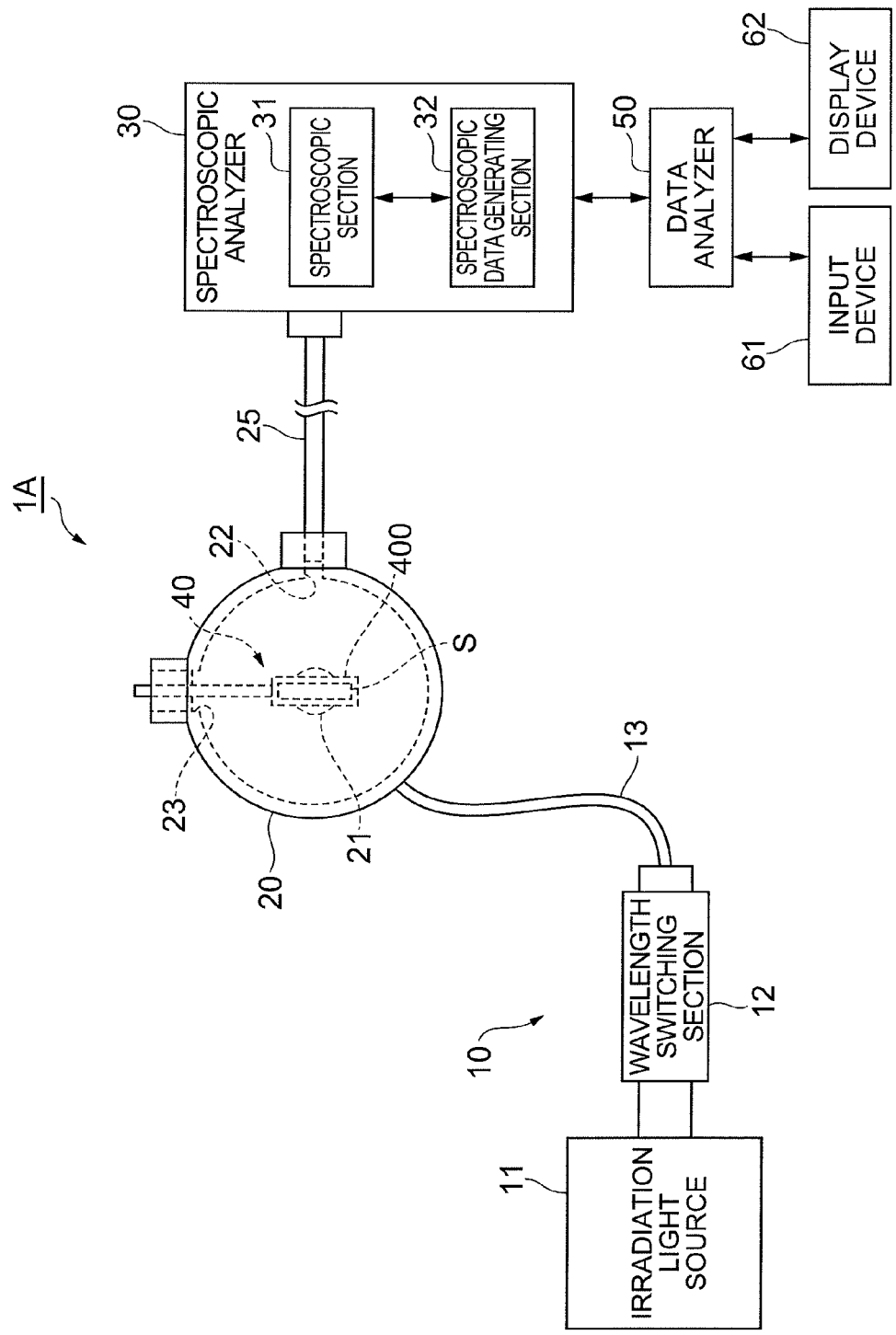
FIG. 1 is a diagram schematically showing a configuration of an embodiment of a spectroscopic measurement apparatus.

Hereinafter, preferred embodiments of a spectroscopic measurement apparatus, a spectroscopic measurement method, and a spectroscopic measurement program according to the present invention will be described in detail with reference to the drawings. In the description of the drawings, the same components are attached with the same reference symbols, and overlapping description will be omitted. Moreover, the dimensional ratios in the drawings are not always equal to those in the description.

FIG. 1 is a diagram schematically showing a configuration of an embodiment of a spectroscopic measurement apparatus according to the present invention. A spectroscopic measurement apparatus 1A in accordance with the present embodiment includes an irradiation light supplying section 10, an integrating sphere 20, a spectroscopic analyzer 30, and a data analyzer 50, and is configured so as to irradiate a sample S such as a luminescent material with excitation light of a predetermined wavelength, and to enable measurement and evaluation of light emission characteristics such as fluorescence characteristics of the sample S by a photoluminescence method.

The irradiation light supplying section 10 is irradiation light supplying means which supplies the excitation light for measuring light emission characteristics of the sample S as irradiation light supplied into the interior of the integrating sphere 20 with the sample S of a measurement object housed. In FIG. 1, the irradiation light supplying section 10 includes an irradiation light source 11, and a light guide 13 for guiding light from the light source 11 to the integrating sphere 20. Further, a wavelength switching section 12 is provided between the irradiation light source 11 and the light guide 13 in the supplying section 10. Thus, the irradiation light supplying section 10 of the present configuration example is configured so that the irradiation light supplying section can switch the irradiation light to the integrating sphere 20 between the excitation light of a predetermined wavelength and light (hereinafter referred to as "white light") containing light components in a predetermined wavelength range, and functions as excitation light supplying means and white light supplying means.

A specific configuration example of the irradiation light supplying section 10 can use a white light source as the irradiation light source 11, and can use wavelength selecting means, which selects only the light component in a predetermined wavelength range of the light supplied from the light source 11 to the light guide 13, in the wavelength switching section 12. In this case, when the wavelength selection is set to OFF in the wavelength switching section 12, the irradiation light to the integrating sphere 20 is the white light, and when the wavelength selection is set to ON, the irradiation light to the integrating sphere 20 is the excitation light of the predetermined wavelength. Specifically, for example, a spectral filter or a spectrometer or the like can be used as the wavelength selecting means.

The integrating sphere 20 is a element used for measurement of the light emission characteristics of the sample S located interior, and has an entrance aperture 21 for inputting the excitation light with which the sample S is irradiated into the integrating sphere 20, an exit aperture 22 for outputting the light to be measured from the sample S to the outside, and a sample introduction opening 23 for carrying sample S inside the integrating sphere 20. A sample holder 40 is fixed to the sample introduction opening 23. Further, a sample container 400 for holding the sample S at a predetermined position in the integrating sphere 20 is provided at the end portion of the sample holder 40.

An output end portion of the light guide 13 for irradiation light input is fixed to the entrance aperture 21 of the integrating sphere 20. For example, an optical fiber can be used as the light guide 13. Further, an input end portion of a light guide 25 for guiding the light to be measured from the sample S to the spectroscopic analyzer 30 in the subsequent stage is fixed to the exit aperture 22 of the integrating sphere 20. For example, a single fiber or a bundle fiber can be used as the light guide 25.

The spectroscopic analyzer 30 is spectroscopic means for dispersing the light to be measured from the sample S exiting through the light guide 25 from the exit aperture 22 of the integrating sphere 20 and for obtaining its wavelength spectrum. In this configuration example, the spectroscopic analyzer 30 is configured as a multi-channel spectrometer having a spectroscopic section 31 and a spectroscopic data generating section 32.

The spectroscopic section 31 includes a spectrometer for dispersing the light to be measured into wavelength components and a photodetector for detecting the light from the spectrometer. For example, a CCD linear sensor with pixels of multi-channels (e.g. 1024 channels) for detecting respective wavelength components of the light to be measured dispersed into wavelength components arranged in one dimension can be used as the photodetector. The measurement wavelength region in the spectroscopic section 31 can be set suitably in accordance with a specific configuration and the like, and for example can be set to 300 nm to 950 nm. Further, the spectroscopic data generating section 32 is spectroscopic data generating means which performs signal processing necessary for detection signals output from respective channels of photodetector of the spectroscopic section 31 and generates wavelength spectrum data as spectroscopic data of the light to be measured. The wavelength spectrum data generated and obtained in the spectral data generating section 32 are output to a data analyzer 50 of the subsequent stage.

The data analyzer 50 is data analyzing means which performs necessary data analysis for the wavelength spectrum obtained by the spectroscopic analyzer 30, to obtain information about the sample S. The specific content of the data analysis in the analyzer 50 is described later. Further, an input device 61 used for inputting instructions about data analysis and the like, inputting analysis conditions, and the like, and a display device 62 used for displaying data analysis results, and the like, are connected to the data analyzer 50.

Figure 2:
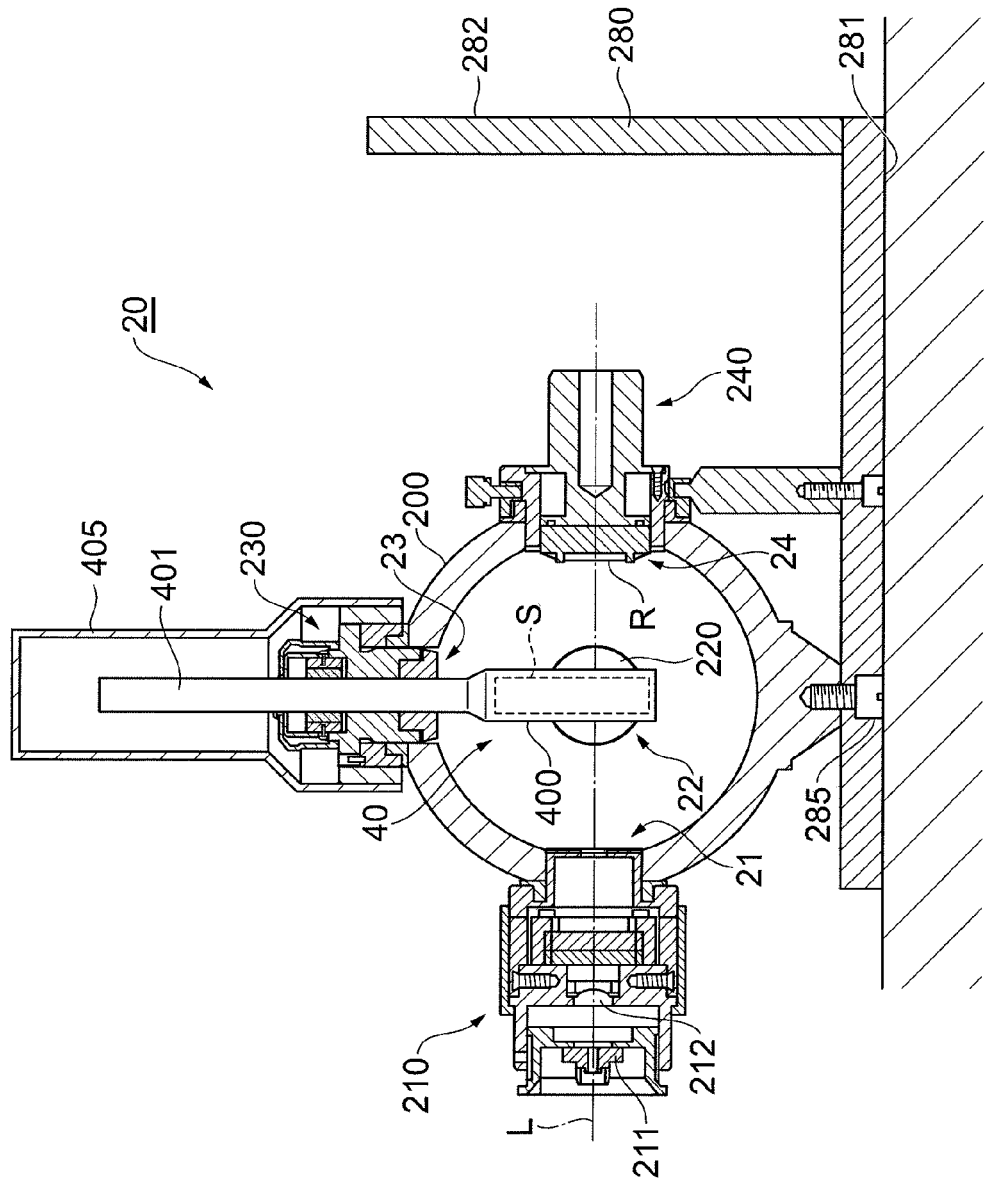
FIG. 2 is a sectional view showing an example of a configuration of an integrating sphere.

FIG. 2 is a sectional view showing an example of a configuration of the integrating sphere 20 used in the spectroscopic measurement apparatus 1A shown in FIG. 1, and shows a sectional structure of the integrating sphere 20 along an irradiation light axis L of the excitation light. The integrating sphere 20 in this configuration example has an integrating sphere body 200 fixed to a mount 280 with an attachment screw 285. Further, the mount 280 is formed in an L-shape having two ground contact surfaces 281, 282 orthogonally intersecting each other. The irradiation optical axis L passes the center position of the integrating sphere body 200, and extends in a direction parallel to the ground contact surface 281 and orthogonal to the ground contact surface 282.

The entrance aperture 21, the exit aperture 22, and the sample introduction opening 23, which are shown in FIG. 1, are provided in the integrating sphere body 200. The entrance aperture 21 is provided at a predetermined position (left side position in the figure) of the integrating sphere body 200 on one side of the optical axis L. Further, the exit aperture 22 is provided at a predetermined position on a plane which passes the center position of the integrating sphere body 200 and is orthogonal to the optical axis L. Further, the sample introduction opening 23 is provided on a plane which passes the center position of the integrating sphere body 200 and is orthogonal to the optical axis L, and at a position (upper side position in the figure) which is off by 90° from the exit aperture 22 as seen from the center position. In addition, in the configuration example shown in FIG. 2, a second sample introduction opening 24 is provided in addition to the opening 23. This sample introduction opening 24 is provided at a position (right side position in the figure) facing the entrance aperture 21 on the other side of the optical axis L.

A light guide holder 210 for connection of the light guide 13 for inputting the irradiation light is inserted and mounted into the entrance aperture 21. A light guide holder 220 for connection of the light guide 25 for outputting the light to be measured is inserted and mounted into the exit aperture 22. Here, illustration of the light guides 13, 25 is omitted in FIG. 2.

A sample holder fixing member 230 for fixing the sample holder 40 is mounted in the first sample introduction opening 23. The sample holder 40 includes a sample container 400 with a hollow space (e.g. quadrangular prism shape) for containing the sample S, and a container supporter 401 extending in a predetermined direction from the sample container 400. The container 400 is fixed to the body 200 via the supporter 401 and the fixing member 230 while being located at the center of the integrating sphere body 200, as shown in FIG. 2. Preferably, the sample container 400 is made of a material through which light including the excitation light and the light to be measured transmits, and an optical cell made of synthetic quartz glass is preferably used, for example. The container supporter 401 is composed of a rod-like branch pipe or the like extending in the shape of a pipe, for example. Further, a second sample holder 240 for setting a sample R is mounted in the second sample introduction opening 24.

The aperture 23 and the sample holder 40 can be preferably used, for example, in the case where the sample S is a solution in which a luminescent material is dissolved. Also, such a sample holder 40 can be used even in the case where the sample S is a solid sample, a powder sample, or the like. The aperture 24 and the sample holder 240 can be preferably used, for example, in the case where the sample R is a solid sample or a powder sample. In this case, a sample holding substrate, a petri dish, or the like can be used as the sample container, for example.

Figure 3:
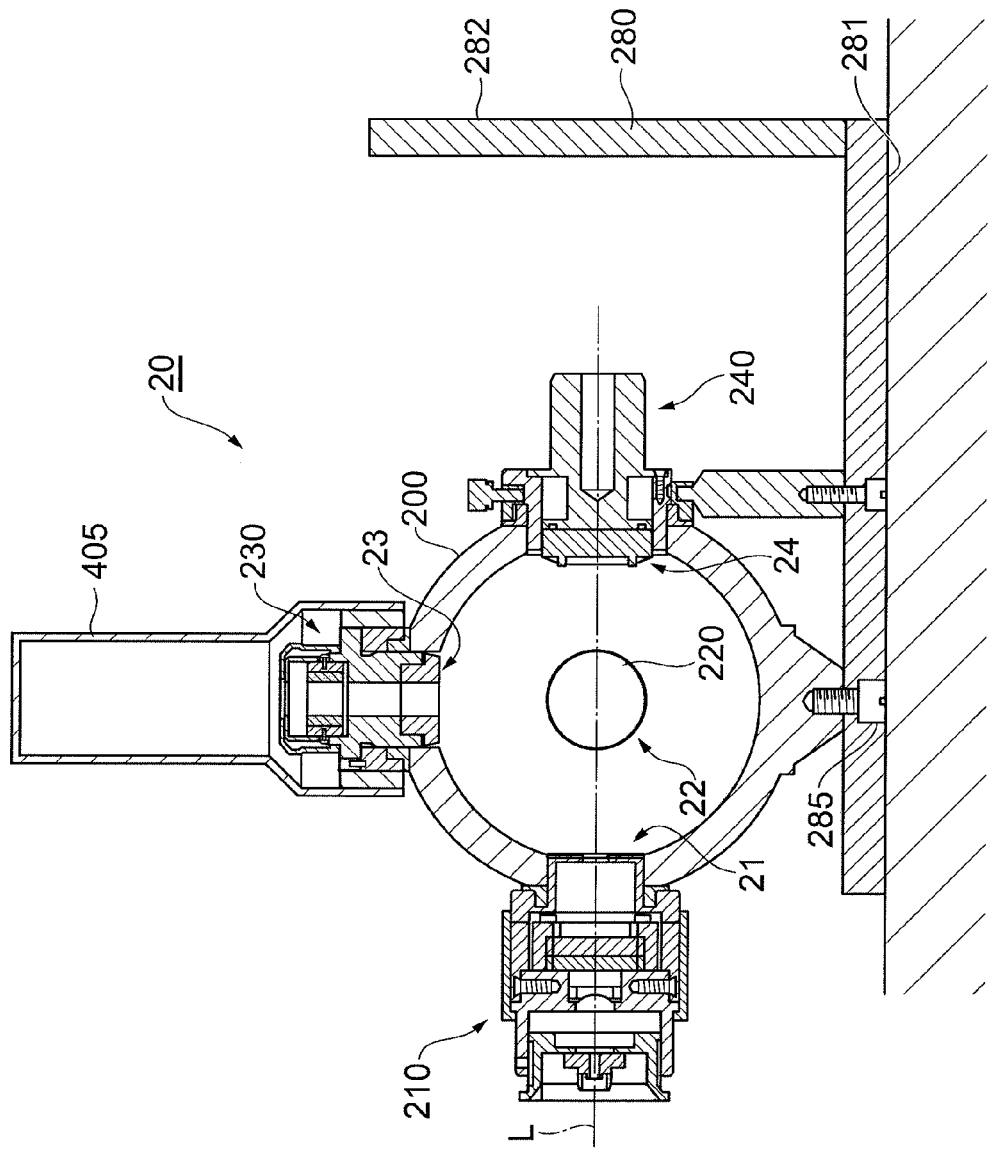
FIG. 3 is a sectional view showing an example of a configuration of the integrating sphere.

The sample holders 40, 240 are selectively used depending on the type of the sample S, the content of spectroscopic measurement, and the like. When the sample holder 40 including the sample container 400 is used, the integrating sphere 20 is set with the grounding surface 281 of the mount 280 down so that the light axis L is along a horizontal line. Also, when the sample holder 240 is used, the integrating sphere 20 is set with the grounding surface 282 of the mount 280 down so that the light axis L is along a vertical line. The following description is mainly for the case where a spectroscopic measurement of the sample S is performed by using the sample holder 40. Further, when a reference measurement is performed without the sample S and the sample container 400 as described later, the measurement is performed with a light shielding cover 405 put on as shown in FIG. 3.

The light guide 13 for inputting the irradiation light is held while being positioned by a light guide holding section 211 of the light guide holder 210. Light from the irradiation light source 11 (see FIG. 1) is guided to the integration sphere 20 by the light guide 13, and the sample S held in the sample container 400 is irradiated with the light, while the light is collected by a condensing lens 212 placed in the light guide holder 210. Further, the light guide 25 for outputting the light to be measured is held while being positioned by the light guide holder 220.

When the excitation light having a predetermined wavelength is supplied as irradiation light from the irradiation light supplying section 10, light from the sample S irradiated with the excitation light is multi-diffusely-reflected by high diffuse reflection powders applied on the inner wall of the integrating sphere body 200. The diffusely-reflected light enters the light guide 25 connected to the light guide holder 220, and is guided to the spectroscopic analyzer 30 as light to be measured. Thus, the spectroscopic measurement of the light to be measured from the sample S is performed. The light from the sample S as the light to be measured includes: light emission such as fluorescence generated at the sample S by irradiation of the excitation light, light components of the excitation light scattered, reflected, and the like at the sample S, and the like.

Figure 4:
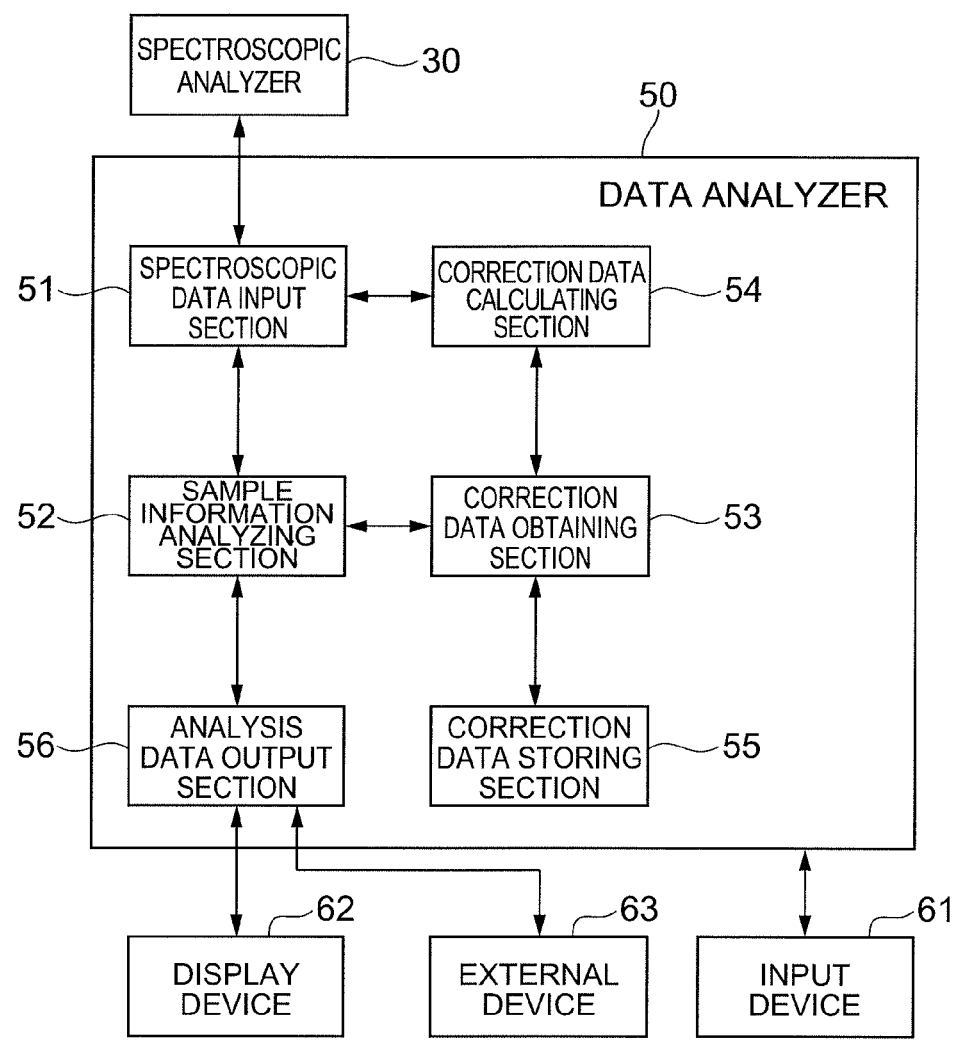
FIG. 4 is a block diagram showing an example of a configuration of a data analyzer.

FIG. 4 is a block diagram showing an example of the configuration of the data analyzer 50 used in the spectroscopic measurement apparatus 1A shown in FIG. 1. The data analyzer 50 of the present configuration example includes a spectroscopic data input section 51, a sample information analyzing section 52, a correction data obtaining section 53, and an analysis data output section 56. Further, in this configuration example of the data analyzer 50, for the correction data obtaining section 53, a correction data calculating section 54 and a correction data storing section 55 are provided.

The spectroscopic data input section 51 is input means for inputting data such as a wavelength spectrum obtained as spectroscopic data by the spectroscopic analyzer 30. The spectroscopic data input from the input section 51 are sent to the sample information analyzing section 52. The analyzing section 52 is sample information analyzing means which analyzes the input wavelength spectrum, and obtains information of the sample S. Further, the correction data obtaining section 53 is correction data obtaining means which considers light absorption caused by the sample container 400, specifically, absorption of at least one of the excitation light and the light emission from the sample S and obtains correction data for correcting the wavelength spectrum, for the above-described configuration where the sample S is held by the sample container 400 in the integrating sphere 20. The analyzing section 52 corrects the wavelength spectrum by using the correction data obtained by the correction data obtaining section 53, analyzes the corrected wavelength spectrum, and obtains information of the sample S such as luminescence quantum yield by the PL method.

The correction data for the wavelength spectrum can be obtained, for example, from the correction data calculating section 54. The calculating section 54 is correction data calculating means which refers to the wavelength spectrum of measurement results for correction data derivation where the measurement is performed under a predetermined condition, and calculates the correction data on the basis of the reference. The specific calculation method for the correction data is described later. In addition, if the correction data of the wavelength spectrum are obtained in advance, the correction data may be stored in the correction data storing section 55, and in accordance with necessity, the correction data obtaining section 53 may read and obtain the correction data. In this case, the correction data calculating section 54 may not be provided. Further, the correction data calculated by the correction data calculating section 54 may be stored in the correction data storing section 55, and in accordance with necessity, the correction data obtaining section 53 may read the correction data.

The analysis data output section 56 is output means for outputting an analysis result of the sample information analyzed by the sample information analyzing section 52. When the analysis result data is output via the output section 56 to the display device 62, the display device 62 displays the analysis result in a predetermined display screen to the operator. Further, the output target of the analysis result is not always the display device 62, and may be another device. In the configuration of FIG. 4, in addition to the display device 62, an external device 63 is connected to the output section 56. The external device 63 is, for example, a printer, an external memory device, or another terminal device.

A process corresponding to the spectroscopic measurement method executed in the data analyzer 50 shown in FIG. 1 and FIG. 4 can be realized by the spectroscopic measurement program for making a computer execute a data analysis for the wavelength spectrum obtained by the spectroscopic analyzer 30 as spectroscopic means. For example, the data analyzer 50 can be configured with a CPU for executing respective software programs necessary for processing spectroscopic measurements, ROM for storing the software programs, and RAM for storing data temporarily while running the program. In such a configuration, the CPU executes a predetermined spectroscopic measurement program, so that the data analyzer 50 and the spectroscopic measurement apparatus 1A described above can be realized.

Furthermore, the above-described program for making a CPU execute each process for spectroscopic measurement can be stored in a computer readable recording medium, and can be distributed. Such a memory medium includes, for example, magnetic media such as a hard disk and flexible disk, optical media such as a CD-ROM and DVD-ROM, magnetooptic media such as a floptical disk, or a hardware device such as a RAM, ROM, semiconductor nonvolatile memory especially prepared so as to execute or store a program instruction.

Effects of the spectroscopic measurement apparatus, spectroscopic measurement method, and spectroscopic measurement program according to the above-described embodiment are described.

In the spectroscopic measurement apparatus 1A, the measurement method, and the measurement program shown in FIG. 1 to FIG. 4, the spectroscopic measurement apparatus 1A includes the integrating sphere 20 which has the aperture 21 for entrance of the excitation light and the aperture 22 for exit of the light to be measured and is configured so as to be able to measure light emission characteristics of the sample S by the PL method, and the spectroscopic analyzer 30 which performs spectroscopic measurement of the light to be measured so that the excitation light and the light emission from the sample S can be separated by the wavelength spectrum. Then, for the sample container 400 holding the sample S in the integrating sphere 20, the analyzer 50 prepares correction data considering the light absorption caused by the sample container, corrects the wavelength spectrum by the correction data, and then performs analysis of the wavelength spectrum and derivation of sample information. This reduces errors caused in the analysis result of the luminescence quantum yield and the like, and allows the spectroscopic measurement for the sample S to be performed preferably and accurately, even in the case where the influence of the sample container 400 on light absorption cannot be disregarded.

Figure 5:
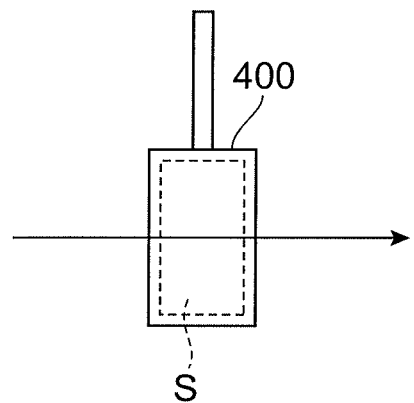
FIG. 5 is a diagram schematically showing light absorption by a sample container.
Figure 5:
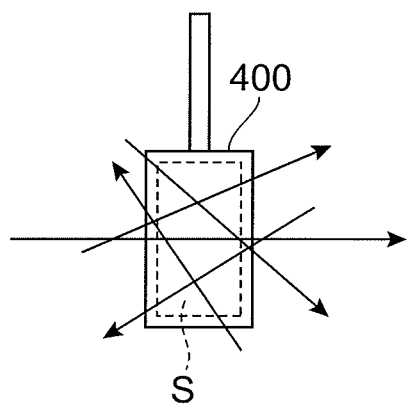

Here, when the integrating sphere 20 is used for spectroscopic measurement of the sample S, the influence of the sample container on light absorption becomes larger than usual measurement as shown in FIG. 5. Specifically, in the usual spectroscopic measurement, light such as excitation light, light to be measured passes in the thickness direction of the sample container 400 only once, as shown in (a) in FIG. 5. In this case, the attenuation of detection intensity I with respect to input intensity $I_0$ by a thickness L of the sample container 400 is:

$$I = I_0 e^{-\mu L}$$

On the other hand, in the spectroscopic measurement apparatus 1A using the integrating sphere 20, as shown in (b) in FIG. 5, the excitation light, or the light emitted from the sample S is multi-reflected by the inner wall of the integrating sphere body 200, to make multiple passes through the sample container 400. In this case, since the whole of a volume V of the sample container 400 contributes to light attenuation, the attenuation of intensity is:

$$I = I_0 e^{-\mu V}$$

so that an influence of light attenuation caused by absorption in the sample container 400 becomes larger.

With respect to this, in the spectroscopic measurement apparatus 1A of the above-described embodiment, the correction data obtaining section 53 obtains correction data considering the light absorption by the sample container 400 from the calculating section 54 or the storing section 55, the sample information analyzing section 52 corrects the wavelength spectrum obtained by the spectroscopic analyzer 30 by using the correction data, and after that, the data analysis for obtaining the sample information is performed. The sample information can be accurately derived by using this configuration. Such a problem of the light absorption caused by a sample container is not at all described for example in the above-described Patent Document 1.

Here, as described above, the irradiation light supplying section 10 for the integrating sphere 20 is preferably configured so as to be able to supply white light in addition to excitation light as irradiation light. Such white light can be used, for example, when correction data considering light absorption by the sample container 400 is obtained by measurement. Further, as for a specific configuration of the irradiation light supplying section 10, a configuration can be used in which, as shown in FIG. 1, a white light source is used as the irradiation light source 11, and the wavelength switching section 12 switches between the excitation light and the white light. Alternatively, two types of light sources of white light source and excitation light source can be used as the irradiation light source. Further, in the case where the white light is not required, only an excitation light source may be used for the irradiation light supplying section 10.

The sample container 400 for holding the sample S is preferably located at the center of the integrating sphere 20 as shown in FIG. 2. In such a configuration, light emission from the sample S can be preferably measured by the symmetrically arranged configuration of the sample S in the integrating sphere 20 and the like. Here, in some cases, the emission pattern of the light emission from the sample S has a certain directionality. On the other hand, the shape of the integrating sphere 20 is not an ideal sphere due to the structure that for example apertures and light shielding sections are formed in the interior. In regard to this, as described above, the spectroscopic measurement using the integrating sphere can bring out most effects by arranging the sample container at the center of the integrating sphere 20. Further, even when performing absorption measurement for the sample container to obtain the correction data, the above-described arrangement is effective for the same reason.

Further, the sample container 400 is preferably made of a material through which the excitation light and the light to be measured transmit. For example, when performing a measurement with the sample S in a solution state contained in a hollow cell, an optical cell transmitting light needs to be used for the sample container. Even in such a configuration, sample information can be obtained with accuracy by using the above-described correction data.

In addition, the above-described configuration can be especially preferably applied to the case where the sample S held in the sample container 400 is a solution sample. Here, when considering high-efficiency luminescent material (fluorescent, phosphorescent material) which is actively investigated in recent years, a problem of deactivation is caused by collision with oxygen and the like existing in the sample and its circumference. Therefore, when evaluating the light emitting efficiency of such a sample, oxygen contained in a sample solution needs to be removed by deaeration. Such a deaeration of the sample can be preferably performed in the configuration of the sample container 400 made of an optical cell as shown in FIG. 2. Further, the sample information such as luminance efficiency can be obtained with accuracy by using the above-described correction data in the configuration using the optical cell.

Figure 6:
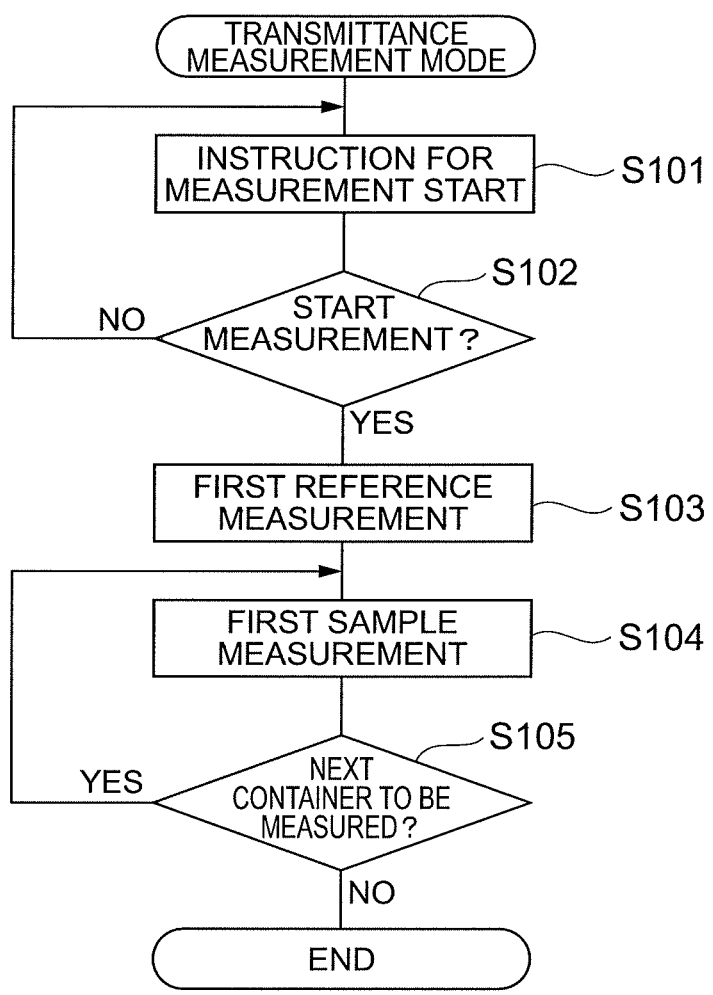
FIG. 6 is a flowchart showing an operation example of the measurement apparatus in a transmittance measurement mode.
Figure 7:
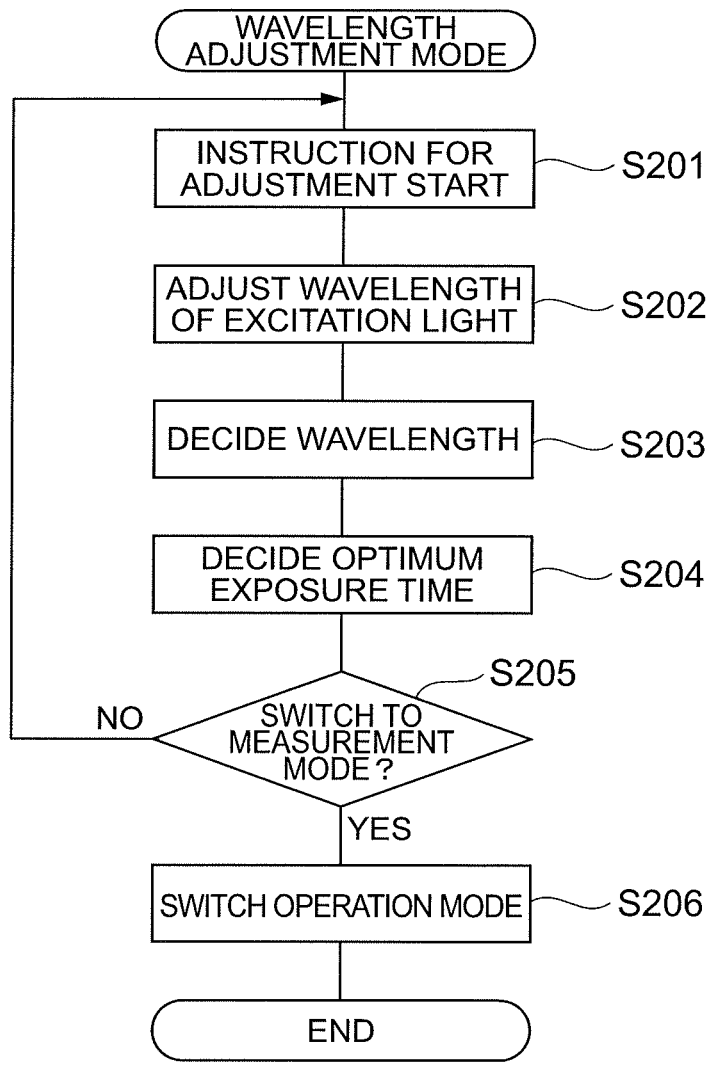
FIG. 7 is a flowchart showing an operation example of the measurement apparatus in a wavelength adjustment mode.
Figure 8:
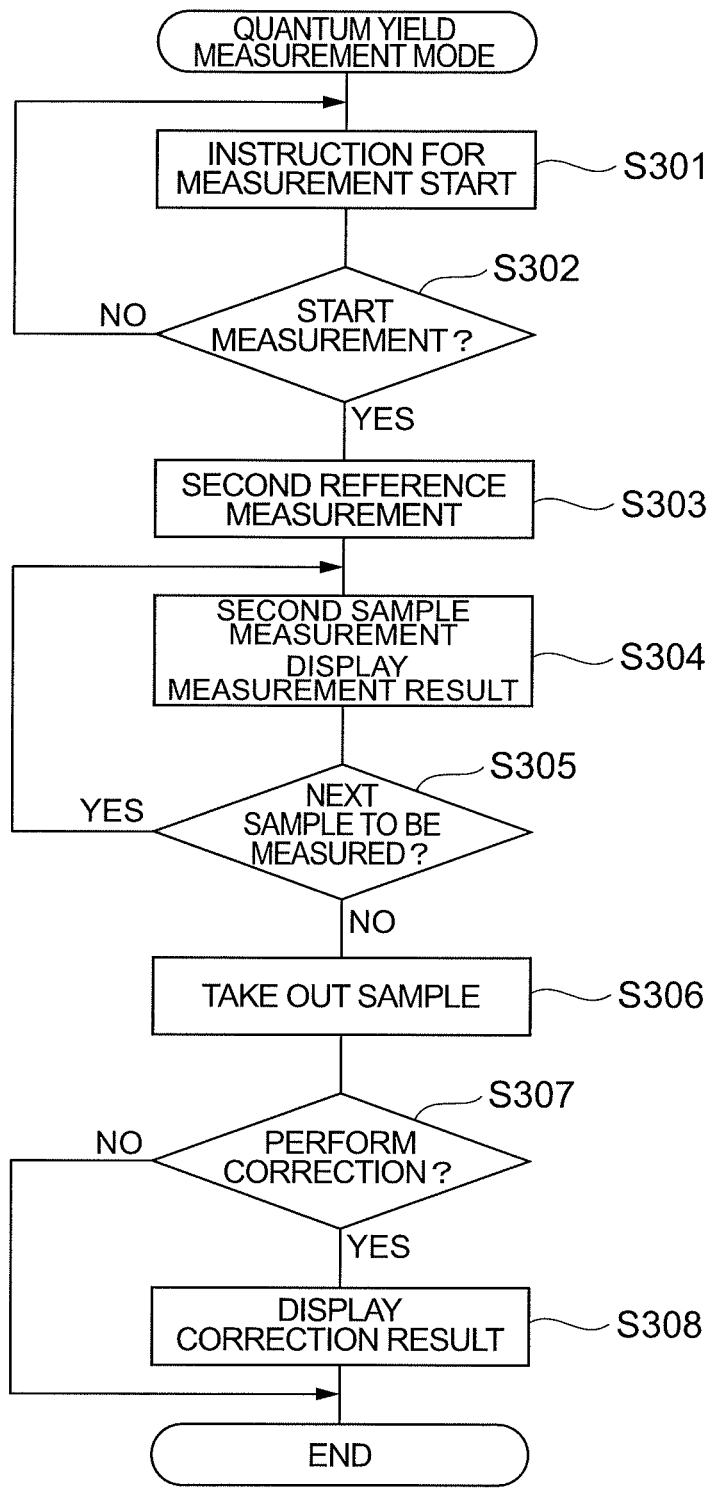
FIG. 8 is a flowchart showing an operation example of the measurement apparatus in a quantum yield measurement mode.

An example of the spectroscopic measurement method using the spectroscopic measurement apparatus 1A of the above-described embodiment is described together with a specific operation example of the spectroscopic measurement apparatus 1A. FIG. 6 is a flowchart showing an operation example of the measurement apparatus in a transmittance measurement mode. FIG. 7 is a flowchart showing an operation example of the measurement apparatus in a wavelength adjustment mode. FIG. 8 is a flowchart showing an operation example of the measurement apparatus in a quantum yield measurement mode.

Further, FIG. 9 to FIG. 12 are graphs showing measurement results of a first reference measurement, a first sample measurement, a second reference measurement, and a second sample measurement described later, and correction results by the correction data. In respective graphs, the horizontal axis shows wavelength λ (nm) of each component of the light to be measured which is wavelength-resolved and detected in the spectroscopic analyzer 30, and the vertical axis shows light emission intensity (detected intensity of the light to be measured) at each wavelength, or light transmittance (graph (b) in FIG. 9) of the sample container. Further, these measurement results are obtained in a case that the sample S is a quinine sulfate 1N sulfuric acid solution, and the sample container 400 is a synthetic silica cell.

First, a transmittance measurement mode is described. The transmittance measurement mode shown in FIG. 6 is an operation mode executed for obtaining correction data of a wavelength spectrum. When calculating the correction data, generally, it is preferable that a first reference measurement of performing a measurement by supplying the white light to the interior of the integrating sphere without the sample and without the sample container, and a first sample measurement of performing a measurement by supplying the white light without the sample and with the sample container are performed, and the correction data considering light absorption by the sample container 400 are calculated on the basis of the wavelength spectra in the measurement results of the first reference measurement and the first sample measurement in the correction data calculating section 54. Thus, separately from the spectroscopic measurement with the sample S, the correction data relating to the light absorption caused by the sample container 400 can be preferably calculated by performing the first reference measurement and the first sample measurement without and with the sample container by using the white light.

In the transmittance measurement mode, in the irradiation light supplying section 10, the irradiation light supplied to the integrating sphere 20 is set to the white light. In this state, when an operator instructs the measurement start by a measurement button or the like (step S101), first, it is confirmed if the first reference measurement will be started (S102), and when the measurement start is available, the interior of the integrating sphere 20 is irradiated with the white light, without both the sample S and the sample container 400, the first reference measurement is performed (S103, first reference measurement step), and the wavelength spectrum $I_R(\lambda)$ is obtained.

Next, the sample holder 40 is set in the integrating sphere 20. Then, the first sample measurement is performed by irradiating the sample container 400 set without the sample S with the white light (S104, first sample measurement step), and the wavelength spectrum $I_S(\lambda)$ is obtained. Subsequently, it is confirmed if the measurement is to be performed for the next sample container (S105), and when the measurement is to be performed, the first sample measurement of the step S104 is repeatedly performed. If all the measurements of the sample containers obtaining correction data are finished, the transmittance measurement is terminated.

The correction data calculating section 54 of the data analyzer 50 calculates the correction data of the wavelength spectrum on the basis of the wavelength spectra $I_R(\lambda)$, $I_S(\lambda)$ obtained by the above-described measurements (correction data calculating step). Specifically, the light transmittance $\gamma(\lambda)$ at each wavelength of the sample container 400 is obtained by:

$$\gamma(\lambda)=I_S(\lambda)/I_R(\lambda)$$

for the wavelength spectrum $I_R(\lambda)$ obtained without the sample container and the wavelength spectrum $I_S(\lambda)$ obtained with the sample container. Also, an equation $$\gamma(\lambda)=1-\beta(\lambda)$$

holds, where the light absorptance of the sample container 400 is $\beta(\lambda)$. The collection data $X(\lambda)$ showing a correction value at each wavelength for the wavelength spectrum considering light absorption by the sample container is calculated by $$X(\lambda)=1/\gamma(\lambda)=1/(1-\beta(\lambda))$$

on the basis of the above-described transmittance $\gamma(\lambda)$ or absorptance $\beta(\lambda)$.

Figure 9:
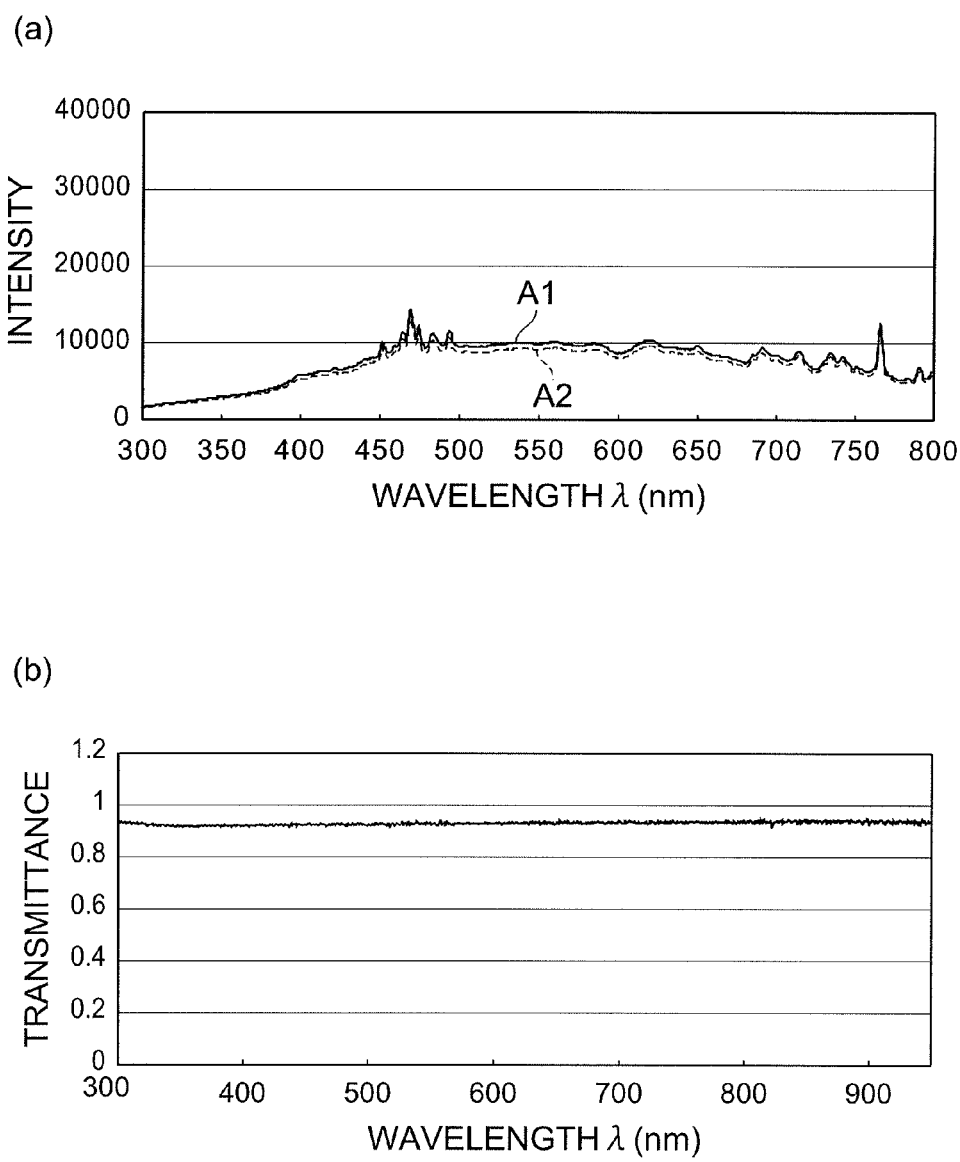
FIG. 9 includes graphs showing measurement results of a first reference measurement and a sample measurement.

Graph (a) in FIG. 9 shows a example of measurement results of the first reference measurement and the first sample measurement, graph A1 shows a wavelength spectrum $I_R(\lambda)$ of the first reference measurement without the sample container, and graph A2 shows a wavelength spectrum $I_S(\lambda)$ of the first sample measurement with the sample container. In the graph A2, the detected intensity is reduced than in the graph A1 by the light absorption at the sample container. Further, Graph (b) in FIG. 9 shows the transmittance $\gamma(\lambda)$ of the sample container obtained by these measurement results. As described above, the correction data can be derived from the transmittance by using the equation $X(\lambda)=1/\gamma(\lambda)$.

Next, a wavelength adjustment mode is described. The wavelength adjustment mode shown in FIG. 7 is an operation mode executed, for example, in the case where, for switching of the irradiation light supplied from the irradiation light supplying section 10 from the white light to the excitation light, a spectrometer is used for wavelength selection in the wavelength switching section 12. Here, when, for example, a spectral filter is used for wavelength selection in the wavelength switching section 12, the irradiation light can be switched by placing the spectral filter on the optical path, therefore, the wavelength adjustment is unnecessary.

In the wavelength adjustment mode, when the operator instructs the adjustment start by an adjustment button or the like (step S201), first, a wavelength of the excitation light is adjusted by adjusting the setting of the spectrometer or the like in the wavelength switching section 12 (S202), to determine its wavelength (S203). Next, by referring to the characteristics and the like of the set excitation light, an optimum exposure time, during which the sample S is irradiated with the excitation light, is determined (S204). Subsequently, it is confirmed if operation mode of the spectroscopic measurement apparatus 1A is switched from the adjustment mode to the measurement mode (S205), and when the switching is instructed, the operation mode is switched to the measurement mode (S206). When the switching is not instructed, the setting of the irradiation condition of the excitation light is repeatedly executed.

Next, a quantum yield measurement mode is described. The quantum yield measurement mode shown in FIG. 8 is an operation mode which is executed when evaluation of the luminescence quantum yield by the PL method is performed for the sample S including, for example, a luminescent material or the like. When measuring the quantum yield, generally, it is preferable that a second reference measurement of performing a measurement by supplying the excitation light to the interior of the integrating sphere without the sample and with the sample container, and a second sample measurement of performing a measurement by supplying the excitation light with the sample and with the sample container are performed, and the information such as the quantum yield of the sample S is obtained on the basis of the wavelength spectra in the measurement results of the second reference measurement and the second sample measurement in the sample information analyzing section 52. Thus, the second reference measurement with the sample container and the second sample measurement with the sample+the sample container are performed by using the excitation light, and from the measurement results, for example, the sample information such as a luminescence quantum yield by the PL method can be preferably obtained.

In the quantum yield measurement mode, in the irradiation light supplying section 10, the irradiation light to the integrating sphere 20 is set to the excitation light. In this state, when the operator instructs the measurement start by a measurement button or the like (step S301), first, it is confirmed if the second reference measurement will be started (S302), and when the measurement start is available, the excitation light is supplied into the integrating sphere 20 without the sample S and with the sample container 400 set, the second reference measurement is performed (S303, second reference measurement step), and the wavelength spectrum $I^R(\lambda)$ is obtained.

Here, in the wavelength spectrum obtained in the spectroscopic measurement of the sample S, an excitation light wavelength range in which reflected light, scattered light and the like of the excitation light are observed is set to $\lambda_1^E \sim \lambda_2^E$ (where $\lambda_1^E < \lambda_2^E$), and a fluorescence wavelength range in which light emissions such as fluorescence from the sample S are observed and which is located in the longer wavelength side than the excitation light wavelength range is set to $\lambda_1^F \sim \lambda_2^F$ (where $\lambda_1^F < \lambda_2^F$). Further, a wavelength spectrum in the excitation light wavelength range obtained by the second reference measurement is set to $I_0^R(\lambda)$, and a wavelength spectrum in the fluorescence wavelength range is set to $I_F^R(\lambda)$.

Next, the sample holder 40 with the sample container 400 holding the sample S is set in the integrating sphere 20. Then, the excitation light is supplied with both the sample S and the sample container 400, the second sample measurement is performed (S304, second sample measurement step), and the wavelength spectrum $I^S(\lambda)$ is obtained. Further, in accordance with necessity, the measurement result is displayed on the display device 62 via the analyzer 50. Further, a wavelength spectrum in the excitation light wavelength range obtained by the second sample measurement is set to $I_0^S(\lambda)$, and a wavelength spectrum in the fluorescence wavelength range is set to $I_F^S(\lambda)$.

Subsequently, it is confirmed if the measurement is to be performed for the next sample (S305), and when the measurement is to be performed, the second sample measurement of the step S304 is repeatedly performed. When all the measurements of the samples S are finished, the sample S is taken out of the integrating sphere 20 (S306). Next, it is confirmed if correction will be performed for the wavelength spectrum obtained in each measurement (S307). When correction execution is instructed, the sample information analyzing section 52 of the analyzer 50 executes correction of the wavelength spectrum related to light absorption caused by the sample container by using the correction data obtained by the correction data obtaining section 53 from the calculating section 54 or the storing section 55, and the correction result is displayed on the display device 62 (S308, correction data obtaining step, sample information analyzing step). With that, the spectroscopic measurement of the sample S in the quantum yield measurement mode is terminated.

Figure 10:
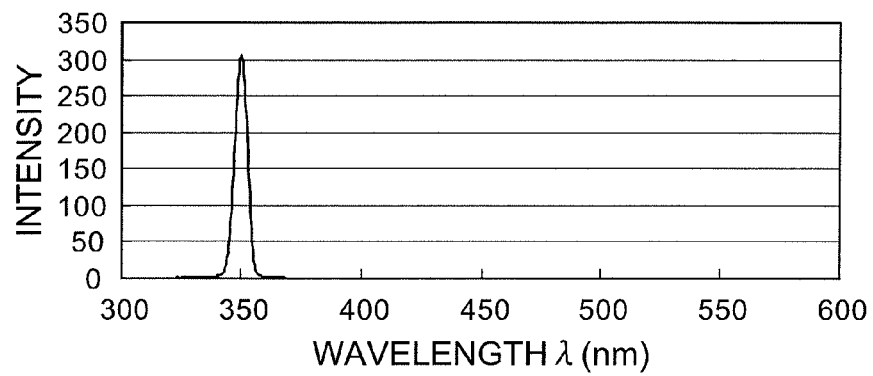
FIG. 10 includes graphs showing measurement results of a second reference measurement and a sample measurement.
Figure 10:
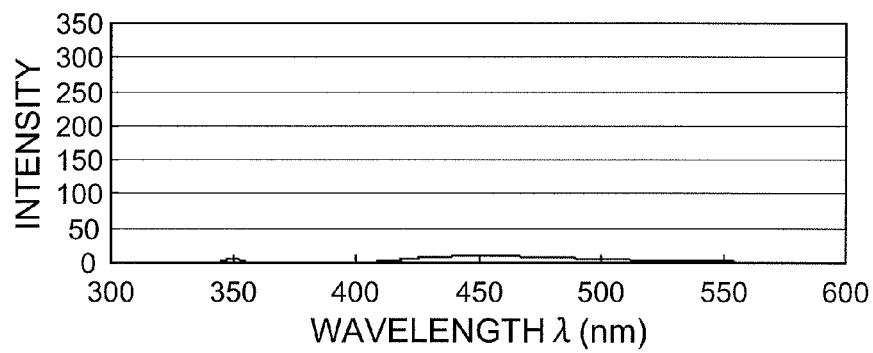

Graphs (a) and (b) in FIG. 10 show an example of measurement results of the second reference measurement and the second sample measurement, graph (a) shows wavelength spectra $I_0^R(\lambda)$, $I_F^R(\lambda)$ of the second reference measurement with the sample container, and graph (b) shows wavelength spectra $I_0^S(\lambda)$, $I_F^S(\lambda)$ of the second sample measurement with both of the sample and the sample container. In the graph (a), an excitation light component is observed in the excitation light wavelength range near a wavelength of 350 nm. Further, in the graph (b), in addition to the excitation light component, a fluorescence component (light emission component) from the sample S is observed in the fluorescence wavelength range in the long wavelength side.

For these wavelength spectra, first, data correction concerning measurement characteristics, detection sensitivity, and the like in the whole of the measurement apparatus is performed. Here, an apparatus factor $cS(\lambda)$ used for the apparatus correction is obtained in advance, and stored in the analyzer 50. The wavelength spectra $I_0^R(\lambda)$ and $I_F^R(\lambda)$ of the second reference measurement are corrected into an excitation light spectrum $I_{ex}^R(\lambda)$ and a fluorescence spectrum $I_{em}^R(\lambda)$ by using the apparatus factor cS, respectively, by $$I_{ex}^R(\lambda) = I_0^R(\lambda) cS(\lambda)$$

$$I_{em}^R(\lambda) = I_F^R(\lambda) cS(\lambda) \qquad \text{[Equation 1]}$$

In the same way, the wavelength spectra $I_0^S(\lambda)$ and $I_F^S(\lambda)$ of the second sample measurement are corrected into an excitation light spectrum $I_{ex}^S(\lambda)$ and a fluorescence spectrum $I_{em}^S(\lambda)$, respectively, by $$I_{ex}^R(\lambda) = I_0^R(\lambda) cS(\lambda)$$

$$I_{em}^R(\lambda) = I_F^R(\lambda) cS(\lambda) \qquad \text{[Equation 2]}$$

In addition, when the apparatus correction is unnecessary, $cS(\lambda)=1$ is used in the above-described equations.

Further, transmittance correction considering light transmission and absorption by the sample container 400 is performed for the wavelength spectra with the apparatus corrections completed, by using a function $X(\lambda)$ showing wavelength dependency of the correction data obtained by the correction data obtaining section 53.

First, the wavelength spectra $I_{ex}^R(\lambda)$ and $I_{em}^R(\lambda)$ of the second reference measurement are corrected into an excitation light spectrum $I_{ex}^{Rc}(\lambda)$ and a fluorescence spectrum $I_{em}^{Rc}(\lambda)$ in which the influences of the sample container on light absorption are removed, respectively, by $$I_{ex}^{Rc}(\lambda) = X(\lambda) I_{ex}^R(\lambda)$$

$$I_{em}^{Rc}(\lambda) = X(\lambda) I_{em}^R(\lambda) \qquad \text{[Equation 3]}$$

with the transmittance correction of the sample container using the correction data $X(\lambda)$.

Figure 11:
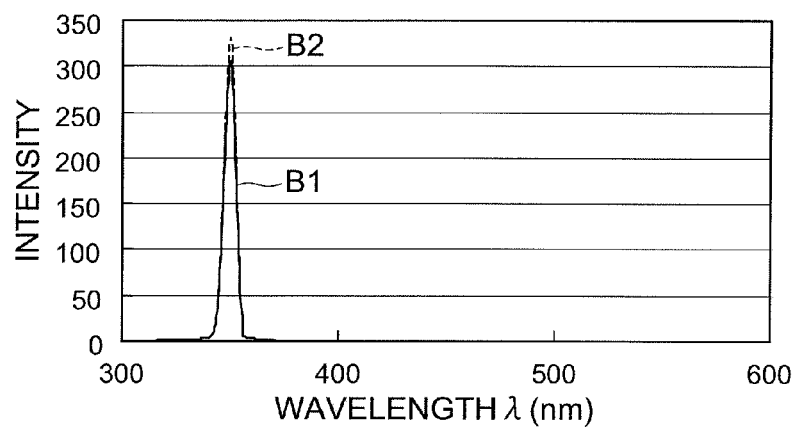
FIG. 11 includes graphs showing the measurement result of the second reference measurement.
Figure 11:
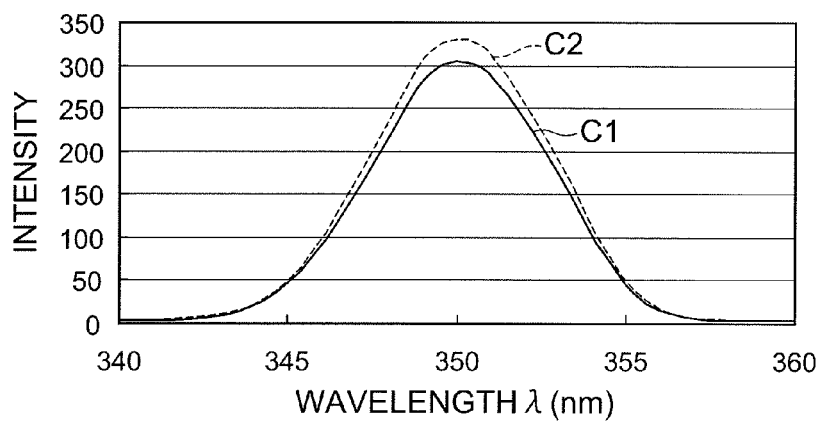

Graph (a) in FIG. 11 shows an example of a wavelength spectrum obtained in the second reference measurement in a wavelength range of 300 nm to 600 nm, and graph (b) shows the same wavelength spectrum in an expanded wavelength range of 340 nm to 360 nm. In these graphs, graphs B1 and C1 show the wavelength spectra $I^R_{ex,em}(\lambda)$ before the transmittance correction by the correction data $X(\lambda)$, and graphs B2 and C2 show the wavelength spectra $I^{Rc}_{ex,em}(\lambda)$ after the transmittance correction. The effect of the transmittance correction can be confirmed by these graphs.

In the same way, the wavelength spectra $I^S_{ex}(\lambda)$ and $I^S_{em}(\lambda)$ of the second sample measurement are corrected into an excitation light spectrum $I^{Sc}_{ex}(\lambda)$ and a fluorescence spectrum $I^{Sc}_{em}(\lambda)$ in which the influences of the sample container on light absorption are removed, respectively, by $$I^{Sc}_{ex}(\lambda)=X(\lambda)I^S_{ex}(\lambda)$$

$$I^{Sc}_{em}(\lambda)=X(\lambda)I^S_{em}(\lambda) \quad \text{[Equation 4]}$$

with the transmittance correction of the sample container using the correction data $X(\lambda)$.

Figure 12:
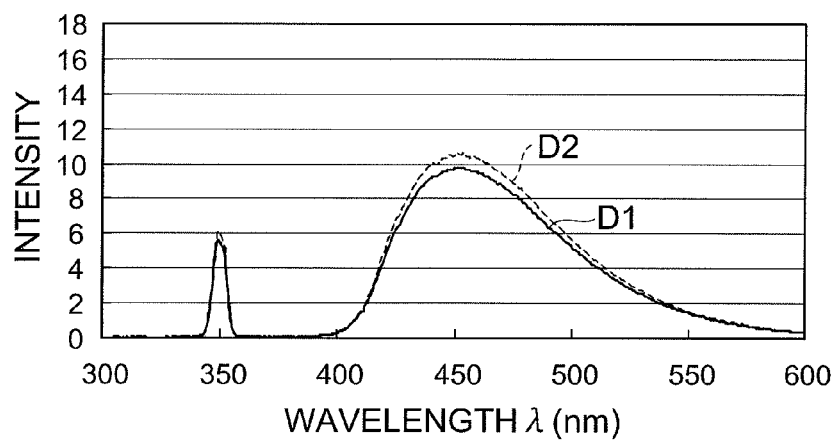
FIG. 12 includes graphs showing the measurement result of the second sample measurement.
Figure 12:
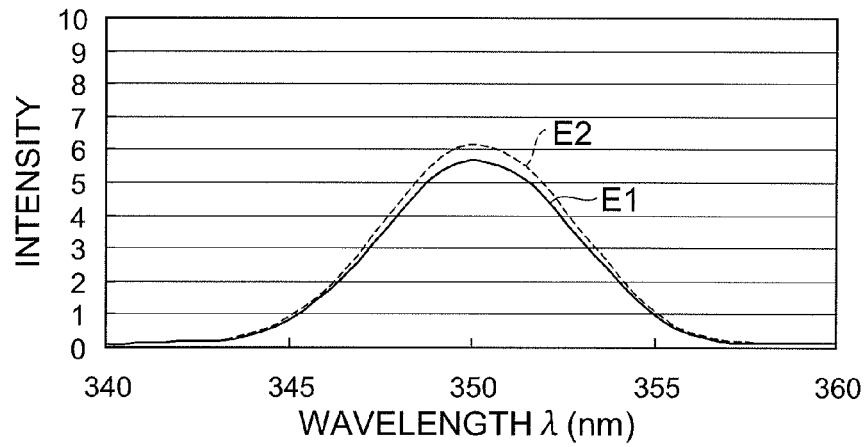

Graph (a) in FIG. 12 shows an example of a wavelength spectrum obtained in the second sample measurement in a wavelength range of 300 nm to 600 nm, and graph (b) shows the same wavelength spectrum in an expanded wavelength range of 340 nm to 360 nm. In these graphs, graphs D1 and E1 show the wavelength spectra $I^S_{ex,em}(\lambda)$ before the transmittance correction, and graphs D2 and E2 show the wavelength spectra $I^{Sc}_{ex,em}(\lambda)$ after the transmittance correction. The effect of the transmittance correction can be confirmed by these graphs in the same way as the second reference measurement.

Fluorescence quantum yield $\phi_f$ in which the influence of light absorption by the sample container is removed and corrected can be obtained by the following equation, by using the corrected wavelength spectra obtained as described above.

$$\Phi_f = \frac{\int_{\lambda 1F}^{\lambda 2F} \{I^{Sc}_{em}(\lambda_F) - I^{Rc}_{em}(\lambda_F)\}d\lambda}{\int_{\lambda 1E}^{\lambda 2E} \{I^{Rc}_{ex}(\lambda_E) - I^{Sc}_{ex}(\lambda_E)\}d\lambda} \quad \text{[Equation 5]}$$

An error of analysis result in the analysis of the quantum yield $\phi_f$ becomes large, especially when the wavelength dependency of the light transmittance $\gamma(\lambda)$ at the sample container is large. With respect to this, analysis accuracy of the quantum yield is improved by performing the correction with the above-described correction data $X(\lambda)$ so that the transmittance becomes constant by cancelling absorption characteristics, absorption band of the sample container or wavelength dependency of the transmittance caused by contamination and the like of the sample container.

As an example of the spectroscopic measurement, spectroscopic measurement and data analysis are performed by using the above-described quinine sulfate 1N sulfuric acid solution as the sample S and the excitation light of wavelength 350 nm, and in the result, the quantum yield obtained from the wavelength spectrum before the correction of the transmittance is $\Phi_f=0.52$, while the quantum yield after the correction of the transmittance is $\Phi_f=0.51$. Thus, the correction considering light absorption by the sample container is performed for the wavelength spectrum, the influence of the sample container on wavelength dependency of the light transmittance and the like is removed, so that the data analysis is performed, and this allows sample information such as quantum yield to be obtained with accuracy.

The fluorescence quantum yield $\phi_f$ is still further described. Generally, fluorescence quantum yield $\phi_f$ is obtained by the following equation.

$$\Phi_f = \frac{\text{the rate of photon emission}}{\text{the rate of absorption}} \quad \text{[Equation 6]}$$

$$= \frac{\int_{\lambda 1F}^{\lambda 2F} F(\lambda)d\lambda}{\int_{\lambda 1E}^{\lambda 2E} I_0(\lambda)\alpha(\lambda)d\lambda}$$

Here, $I_0(\lambda)$ shows irradiation light intensity in photon number unit (photons s$^{-1}$ nm$^{-1}$), $F(\lambda)$ shows fluorescence intensity (photons s$^{-1}$ nm$^{-1}$), and $\alpha(\lambda)$ shows the light absorptance by the sample S.

When the above-described second reference measurement and the sample measurement are performed to obtain the quantum yield $\phi_f$, apparent wavelength spectra $I_0^R(\lambda)$, $I_0^S(\lambda)$ in the excitation light wavelength range obtained by the reference measurement and the sample measurement are respectively as follows.

$$I_0^R(\lambda)=I_0(\lambda)\{1-\beta(\lambda)\}R(\lambda)C(\lambda)$$

$$I_0^S(\lambda)=I_0(\lambda)\{1-\alpha(\lambda)\}\{1-\beta(\lambda)\}R(\lambda)C(\lambda) \quad \text{[Equation 7]}$$

Further, apparent wavelength spectra $I_F^R(\lambda)$, $I_F^S(\lambda)$ in the fluorescence wavelength range are respectively as follows.

$$I_F^R(\lambda)=I_0(\lambda)\{1-\beta(\lambda)\}R(\lambda)C(\lambda)$$

$$I_F^S(\lambda)=F(\lambda)\{1-\beta(\lambda)\}R(\lambda)C(\lambda) \quad \text{[Equation 8]}$$

Here, $R(\lambda)$ shows the transmittance of the integrating sphere at wavelength $\lambda$, $C(\lambda)$ shows the spectral sensitivity of the measurement system, and $\beta(\lambda)$ shows the light absorptance by the optical cell of the sample container. Further, $C(\lambda)$ includes influences of all elements of the measurement system such as a spectrometer, photodetector, and optical fiber. The apparatus factor $cS(\lambda)$ used for the apparatus correction is obtained by $$cS(\lambda)=1/\{R(\lambda)C(\lambda)\} \quad \text{[Equation 9]}$$

based on $R(\lambda)$, $C(\lambda)$.

These wavelength spectra obtained by the spectroscopic analyzer 30 become respectively wavelength spectra $I_{ex}^R(\lambda)$, $I_{ex}^S(\lambda)$, $I_{em}^R(\lambda)$, $I_{em}^S(\lambda)$ shown by $$I_{ex}^R(\lambda) = I_0^R(\lambda)cS(\lambda) \quad \text{[Equation 10]}$$
$$= \frac{I_0^R(\lambda)}{R(\lambda)C(\lambda)}$$
$$= I_0(\lambda)\{1-\beta(\lambda)\}$$

$$I_{ex}^S(\lambda) = I_0^S(\lambda)cS(\lambda)$$
$$= \frac{I_0^S(\lambda)}{R(\lambda)C(\lambda)}$$
$$= I_0(\lambda)\{1-\alpha(\lambda)\}\{1-\beta(\lambda)\}$$

$$I_{em}^R(\lambda) = I_F^R(\lambda)cS(\lambda) \quad \text{[Equation 11]}$$
$$= \frac{I_F^R(\lambda)}{R(\lambda)C(\lambda)}$$
$$= I_0(\lambda)\{1-\beta(\lambda)\}$$

$$I_{em}^S(\lambda) = I_F^S(\lambda)cS(\lambda)$$
$$= \frac{I_F^S(\lambda)}{R(\lambda)C(\lambda)}$$
$$= F(\lambda)\{1-\beta(\lambda)\}$$

after the apparatus correction.

Furthermore, in view of the fact that the correction data is $X(\lambda)=1/(1-\beta(\lambda))$, the wavelength spectra in photon number unit $I_{ex}^{Rc}(\lambda)$, $I_{ex}^{Sc}(\lambda)$, $I_{em}^{Rc}(\lambda)$, $I_{em}^{Sc}(\lambda)$ after the correction by the correction data $X(\lambda)$ considering light absorption by the sample container become respectively $$I_{ex}^{Rc}(\lambda) = X(\lambda)I_{ex}^{R}(\lambda) \qquad \text{[Equation 12]}$$
$$= \frac{I_{ex}^{R}(\lambda)}{\{1-\beta(\lambda)\}}$$
$$= I_0(\lambda)$$

$$I_{ex}^{Sc}(\lambda) = X(\lambda)I_{ex}^{S}(\lambda)$$
$$= \frac{I_{ex}^{S}(\lambda)}{\{1-\beta(\lambda)\}}$$
$$= I_0(\lambda)\{1-\alpha(\lambda)\}$$

$$I_{em}^{Rc}(\lambda) = X(\lambda)I_{em}^{R}(\lambda) \qquad \text{[Equation 13]}$$
$$= \frac{I_{em}^{R}(\lambda)}{\{1-\beta(\lambda)\}}$$
$$= I_0(\lambda)$$

$$I_{em}^{Sc}(\lambda) = X(\lambda)I_{em}^{S}(\lambda)$$
$$= \frac{I_{em}^{S}(\lambda)}{\{1-\beta(\lambda)\}}$$
$$= F(\lambda)$$

In the result, the fluorescence quantum yield $\phi_f$ is obtained by the following equation.

$$\frac{\int_{\lambda 1F}^{\lambda 2F}\{I_{em}^{Sc}(\lambda_F)-I_{em}^{Rc}(\lambda_F)\}d\lambda}{\int_{\lambda 1E}^{\lambda 2E}\{I_{ex}^{Rc}(\lambda_E)-I_{ex}^{Sc}(\lambda_E)\}d\lambda} = \qquad \text{[Equation 14]}$$

$$\frac{\int_{\lambda 1F}^{\lambda 2F}F(\lambda)d\lambda - \int_{\lambda 1F}^{\lambda 2F}I_0(\lambda)d\lambda}{\int_{\lambda 1E}^{\lambda 2E}I_0(\lambda)\alpha(\lambda)d\lambda} \approx \frac{\int_{\lambda 1F}^{\lambda 2F}F(\lambda)d\lambda}{\int_{\lambda 1E}^{\lambda 2E}I_0(\lambda)\alpha(\lambda)d\lambda} = \Phi_f$$

The spectroscopic measurement apparatus, spectroscopic measurement method, and spectroscopic measurement program according to the present invention are not limited to the above-described embodiments and configuration examples, and can be modified in many ways. For example, the integrating sphere 20 and the sample container 400 shown in FIG. 1 and FIG. 2 show an example of the configurations of an integrating sphere and a sample container used in a spectroscopic measurement for a sample S, therefore, if applicable to the above-described analysis method, various configurations can be specifically used.

Also, various configurations other than the spectroscopic analyzer 30 shown in FIG. 1 can be used for spectroscopic means for obtaining a wavelength spectrum of light to be measured. For example, the spectroscopic section 31 and the spectroscopic data generating section 32 configuring the spectroscopic analyzer 30 may have a configuration with them as separate units. Further, other various configurations than the irradiation light supplying section 10 shown in FIG. 1 can be used as irradiation light supplying means for supplying white light and excitation light. In addition, in the above-described embodiment, the above-described correction of the wavelength spectrum is performed in the whole wavelength range, but for example, the correction may be performed only in one of the excitation light wavelength range and the fluorescence wavelength range.

Here, the spectroscopic measurement apparatus of the above-described embodiment comprises: (1) an integrating sphere in which a sample as a measurement object is located, and which has an entrance aperture for inputting excitation light with which the sample is irradiated, and an exit aperture for outputting light to be measured from the sample; (2) irradiation light supplying means which supplies the excitation light as irradiation light supplied via the entrance aperture to the interior of the integrating sphere; (3) a sample container which holds the sample at a predetermined position in the interior of the integrating sphere; (4) spectroscopic means which disperses the light to be measured output from the exit aperture of the integrating sphere and which obtains its wavelength spectrum; and (5) data analyzing means which performs data analysis of the wavelength spectrum obtained by the spectroscopic means, wherein (6) the data analyzing means includes: correction data obtaining means which obtains correction data to correct the wavelength spectrum by considering absorption of at least one of the excitation light and the light to be measured by the sample container; and sample information analyzing means which obtains information of the sample by correcting the wavelength spectrum with the correction data and analyzing the corrected wavelength spectrum.

Further, the spectroscopic measurement method of the above-described embodiment uses the spectroscopic measurement apparatus including: (1) an integrating sphere in which a sample as a measurement object is located, and which has an entrance aperture for inputting excitation light with which the sample is irradiated, and an exit aperture for outputting light to be measured from the sample; (2) irradiation light supplying means which supplies the excitation light as irradiation light supplied via the entrance aperture to the interior of the integrating sphere; (3) a sample container which holds the sample at a predetermined position in the interior of the integrating sphere; and (4) spectroscopic means which disperses the light to be measured output from the exit aperture of the integrating sphere and which obtains its wavelength spectrum, wherein (5) the spectroscopic measurement method performs data analysis of the wavelength spectrum obtained by the spectroscopic means, and comprises: (6) a correction data obtaining step of obtaining correction data to correct the wavelength spectrum by considering absorption of at least one of the excitation light and the light to be measured by the sample container; and a sample information analyzing step of obtaining information of the sample by correcting the wavelength spectrum with the correction data and analyzing the corrected wavelength spectrum.

Further, the spectroscopic measurement program of the above-described embodiment is applied to the spectroscopic measurement apparatus including: (1) an integrating sphere in which a sample as a measurement object is located, and which has an entrance aperture for inputting excitation light with which the sample is irradiated, and an exit aperture for outputting light to be measured from the sample; (2) irradiation light supplying means which supplies the excitation light as irradiation light supplied via the entrance aperture to the interior of the integrating sphere; (3) a sample container which holds the sample at a predetermined position in the interior of the integrating sphere; and (4) spectroscopic means which disperses the light to be measured output from the exit aperture of the integrating sphere and which obtains its wavelength spectrum, wherein (5) the program makes a computer execute data analysis of the wavelength spectrum obtained by the spectroscopic means, and makes the computer execute: (6) a correction data obtaining process of obtaining correction data to correct the wavelength spectrum by considering absorption of at least one of the excitation light and the light to be measured by the sample container; and a sample information analyzing process of obtaining information of the sample by correcting the wavelength spectrum with the correction data and analyzing the corrected wavelength spectrum.

The irradiation light supplying means for supplying the irradiation light into the interior of the integrating sphere is preferably configured so as to be able to supply white light containing light components in a predetermined wavelength range as the irradiation light, in addition to the excitation light of a predetermined wavelength. Such white light can be used to obtain the correction data of the wavelength spectrum considering the light absorption caused by the sample container by measurement.

In this case, in the spectroscopic measurement apparatus, the data analyzing means preferably includes correction data calculating means calculating the correction data on the basis of a measurement result of a first reference measurement of performing a measurement by supplying the white light to the interior of the integrating sphere without the sample and without the sample container, and a measurement result of a first sample measurement of performing a measurement by supplying the white light to the interior of the integrating sphere without the sample and with the sample container.

In the same way, the spectroscopic measurement method preferably comprises a first reference measurement step of performing a measurement by supplying the white light to the interior of the integrating sphere without the sample and without the sample container; a first sample measurement step of performing a measurement by supplying the white light to the interior of the integrating sphere without the sample and with the sample container; and a correction data calculating step of calculating the correction data on the basis of measurement results of the first reference measurement step and the first sample measurement step.

In the same way, the spectroscopic measurement program preferably makes the computer execute a correction data calculating process of calculating the correction data on the basis of a measurement result of a first reference measurement of performing a measurement by supplying the white light to the interior of the integrating sphere without the sample and without the sample container, and a measurement result of a first sample measurement of performing a measurement by supplying the white light to the interior of the integrating sphere without the sample and with the sample container.

In this way, the correction data for light absorption by the sample container can be preferably calculated, by performing the first reference measurement and the first sample measurement without and with the sample container by using the white light, separately from the spectroscopic measurement for the sample. In this case, the correction data obtaining means obtains the correction data from the correction data calculating means. Further, for obtaining the correction data, the correction data calculated in advance may be stored in correction data storing means.

In addition, in the spectroscopic measurement apparatus, the sample information analyzing means preferably obtains information of the sample on the basis of a measurement result of a second reference measurement of performing a measurement by supplying the excitation light to the interior of the integrating sphere without the sample and with the sample container, and a measurement result of a second sample measurement of performing a measurement by supplying the excitation light to the interior of the integrating sphere with the sample and with the sample container.

In the same way, the spectroscopic measurement method preferably comprises a second reference measurement step of performing a measurement by supplying the excitation light to the interior of the integrating sphere without the sample and with the sample container; and a second sample measurement step of performing a measurement by supplying the excitation light to the interior of the integrating sphere with the sample and with the sample container; wherein, in the sample information analyzing step, information of the sample is obtained on the basis of measurement results of the second reference measurement step and the second sample measurement step.

In the same way, in the spectroscopic measurement program, the sample information analyzing process preferably obtains information of the sample on the basis of a measurement result of a second reference measurement of performing a measurement by supplying the excitation light to the interior of the integrating sphere without the sample and with the sample container, and a measurement result of a second sample measurement of performing a measurement by supplying the excitation light to the interior of the integrating sphere with the sample and with the sample container.

Thus, the second reference measurement with the sample container and the second sample measurement with the sample+the sample container are performed by using the excitation light, and from the results, the sample information such as the luminescence quantum yield by the PL method can be preferably obtained.

In addition, the sample container for holding the sample is preferably located at the center of the integrating sphere. In such a configuration, light emission from the sample can be preferably measured generally by the symmetrical arrangement configuration of the sample in the integrating sphere and the like. Further, the sample container is preferably made of a material through which the excitation light and the light to be measured is transmitted. Even in such a configuration, the sample information can be obtained accurately by using the above-described correction data. In addition, the above-described configuration can be preferably applied even to the case where the sample held in the sample container is a solution sample.

INDUSTRIAL APPLICABILITY

The present invention can be used as a spectroscopic measurement apparatus, a measurement method, and a measurement program which can preferably perform spectroscopic measurement of a sample held by a sample container in an integrating sphere.

REFERENCE SIGNS LIST

1A—spectroscopic measurement apparatus, 10—irradiation light supplying section, 11—irradiation light source, 12—wavelength switching section, 13—light guide, 20—integrating sphere, 200—integrating sphere body, 21—entrance aperture, 210—light guide holder, 22—exit aperture, 220—light guide holder, 23, 24—sample introduction opening, 230—sample holder fixing member, 240—sample holder, 25—light guide, 30—spectroscopic analyzer, 31—spectroscopic section, 32—spectroscopic data generating section, 40—sample holder, 400—sample container, 401—container supporter, 50—data analyzer, 51—spectroscopic data input section, 52—sample information analyzing section, 53—correction data obtaining section, 54—correction data calculating section, 55—correction data storing section, 56—analysis data output section, 61—input device, 62—display device, 63—external device.

The invention claimed is:

1. A spectroscopic measurement apparatus comprising:
an integrating sphere in which a sample as a measurement object is located, and having an entrance aperture for inputting excitation light with which the sample is irradiated, and an exit aperture for outputting light to be measured from the sample;
irradiation light supplying means supplying the excitation light as irradiation light supplied via the entrance aperture to the interior of the integrating sphere;
a sample container holding the sample at a predetermined position in the interior of the integrating sphere;
spectroscopic means dispersing the light to be measured output from the exit aperture of the integrating sphere and obtaining a wavelength spectrum; and
data analyzing means performing data analysis of the wavelength spectrum obtained by the spectroscopic means; wherein
the irradiation light supplying means is configured so as to be able to supply white light as the irradiation fiat in addition to the excitation light, so that the irradiation light supplying means can switch the irradiation light to the integrating sphere between the excitation light and the white light, and wherein
the data analyzing means includes:
correction data obtaining means obtaining correction data for correcting the wavelength spectrum by considering absorption of at least one of the excitation light and the light to be measured by the sample container;
sample information analyzing means obtaining information of the sample by correcting the wavelength spectrum with the correction data and analyzing the corrected wavelength spectrum; and
correction data calculating means calculating the correction data, showing a correction value at each wavelength for the wavelength spectrum, on the basis of a measurement result of a first reference measurement of performing a measurement by supplying the white light to the interior of the integrating sphere without the sample and without the sample container, and a measurement result of a first sample measurement of performing a measurement by supplying the white light to the interior of the integrating sphere without the sample and with the sample container.

2. The spectroscopic measurement apparatus according to claim 1, wherein the sample information analyzing means obtains information of the sample on the basis of a measurement result of a second reference measurement of performing a measurement by supplying the excitation light to the interior of the integrating sphere without the sample and with the sample container, and a measurement result of a second sample measurement of performing a measurement by supplying the excitation light to the interior of the integrating sphere with the sample and with the sample container.

3. The spectroscopic measurement apparatus according to claim 1, wherein the sample container is located at the center of the integrating sphere.

4. The spectroscopic measurement apparatus according to claim 1, wherein the sample container is made of a material through which the excitation light and the light to be measured transmit.

5. A spectroscopic measurement method using a spectroscopic measurement apparatus including:
an integrating sphere in which a sample as a measurement object is located, and having an entrance aperture for inputting excitation light with which the sample is irradiated, and an exit aperture for outputting light to be measured from the sample;
irradiation light supplying means supplying the excitation light as irradiation light supplied via the entrance aperture to the interior of the integrating sphere;
a sample container holding the sample at a predetermined position in the interior of the integrating sphere; and
spectroscopic means dispersing the light to be measured output from the exit aperture of the integrating sphere and obtaining a wavelength spectrum,
wherein the irradiation light supplying means is configured so as to be able to supply white light as the irradiation light in addition to the excitation light, so that the irradiation light supplying means can switch the irradiation light to the integrating sphere between the excitation light and the white light, and
wherein the spectroscopic measurement method performs data analysis of the wavelength spectrum obtained by the spectroscopic means, and comprises;
a correction data obtaining step of obtaining correction data for correcting the wavelength spectrum by considering absorption of at least one of the excitation light and the light to be measured by the sample container;
a sample information analyzing step of obtaining information of the sample by correcting the wavelength spectrum with the correction data and analyzing the corrected wavelength spectrum;
a first reference measurement step of performing a measurement by supplying the white light to the interior of the integrating sphere without the sample and without the sample container;
a first sample measurement step of performing a measurement by supplying the white light to the interior of the integrating sphere without the sample and with the sample container; and
a correction data calculating step of calculating the correction data, showing a correction value at each wavelength for the wavelength spectrum, on the basis of measurement results of the first reference measurement step and the first sample measurement step.

6. The spectroscopic measurement method according to claim 5 comprising:
a second reference measurement step of performing a measurement by supplying the excitation light to the interior of the integrating sphere without the sample and with the sample container; and
a second sample measurement step of performing a measurement by supplying the excitation light to the interior of the integrating sphere with the sample and with the sample container; wherein
in the sample information analyzing step, information of the sample is obtained on the basis of measurement results of the second reference measurement step and the second sample measurement step.

7. The spectroscopic measurement method according to claim 5, wherein the sample container is located at the center of the integrating sphere.

8. The spectroscopic measurement method according to claim 5, wherein the sample container is made of a material through which the excitation light and the light to be measured transmit.

9. The spectroscopic measurement method according to claim 5, wherein the sample held by the sample container is a solution sample.

10. A non-transitory computer-readable storage medium having embodied thereon a spectroscopic measurement program being applied to a spectroscopic measurement apparatus including:
- an integrating sphere in which a sample as a measurement object is located, and having an entrance aperture for inputting excitation light with which the sample is irradiated, and an exit aperture for outputting light to be measured from the sample;
- irradiation light supplying means supplying the excitation light as irradiation light supplied via the entrance aperture to the interior of the integrating sphere;
- a sample container holding the sample at a predetermined position in the interior of the integrating sphere; and
- spectroscopic means dispersing the light to be measured output from the exit aperture of the integrating sphere and obtaining a wavelength spectrum,
- wherein the irradiation light supplying means is configured so as to be able to supply white light as the irradiation light in addition to the excitation light, so that the irradiation light supplying means can switch the irradiation light to the integrating sphere between the excitation light and the white light, and
- wherein the program makes a computer execute data analysis of the wavelength spectrum obtained by the spectroscopic means, and makes the computer execute:
- a correction data obtaining process of obtaining correction data for correcting the wavelength spectrum by considering absorption of at least one of the excitation light and the light to be measured by the sample container;
- a sample information analyzing process of obtaining information of the sample by correcting the wavelength spectrum with the correction data and analyzing the corrected wavelength spectrum; and
- a correction data calculating process of calculating the correction data, showing a correction value at each wavelength for the wavelength spectrum, on the basis of a measurement result of a first reference measurement of performing a measurement by supplying the white light to the interior of the integrating sphere without the sample and without the sample container, and a measurement result of a first sample measurement of performing a measurement by supplying the white light to the interior of the integrating sphere without the sample and with the sample container.

11. The non-transitory computer-readable storage medium according to claim 10, wherein the sample information analyzing process obtains information of the sample on the basis of a measurement result of a second reference measurement of performing a measurement by supplying the excitation light to the interior of the integrating sphere without the sample and with the sample container, and a measurement result of a second sample measurement of performing a measurement by supplying the excitation light to the interior of the integrating sphere with the sample and with the sample container.

* * * * *